United States Patent [19]

Cantarelli et al.

[11] Patent Number: 4,587,248
[45] Date of Patent: May 6, 1986

[54] 4-ALKYL-THIOPHENYL-ETHANOLA-MINES, HAVING AN ACTIVITY THE CEREBRAL CIRCULATION, THE BLOOD PLATELET-AGGREGATION AND THE LIPENIA

[76] Inventors: Giorgio Cantarelli, Via Gozzano 4; Giampaolo Picciola, P. le Baracca 6; Franco Ravenna, Via Vincenzo Monti 57/A, all of Milan; Mario Riva, Via Monteverdi 21, Monza(Milan), all of Italy

[21] Appl. No.: 382,649

[22] Filed: May 27, 1982

[30] Foreign Application Priority Data

May 27, 1981 [IT] Italy ............................. 21998 A/81
Feb. 17, 1982 [IT] Italy ............................. 19693 A/82

[51] Int. Cl.$^4$ ................. A61K 31/495; C07D 241/04
[52] U.S. Cl. ................................ 514/255; 514/647; 514/653; 544/391; 544/401; 564/307; 564/343; 564/363
[58] Field of Search ............. 542/440, 470; 544/391, 544/401; 514/255

[56] References Cited

U.S. PATENT DOCUMENTS 3,954,417  5/1976  Roba et al. ....................... 424/250

FOREIGN PATENT DOCUMENTS 2224148  10/1974  France .
1390748  4/1975  United Kingdom .
2025417  1/1980  United Kingdom .

OTHER PUBLICATIONS

Cantarelli, et al., "Chemical Abstracts", vol. 98, 1983, col. 98:179414m.

Primary Examiner—Glennon H. Hollrah
Assistant Examiner—James H. Turnipseed
Attorney, Agent, or Firm—Cushman, Darby & Cushman

[57] ABSTRACT 4-alkyl-thiophenyl-ethanolamines are disclosed, which are compounds having a therapeutical activity against blood-platelet aggregation, and against lipemia and improving the cerebral circulation, said ethanolamines having the general formula:

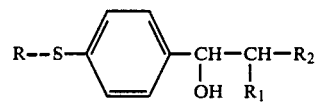

wherein R and $R_1$ are alkyl substituents and $R_2$ is a substituent having an amine character. Due to the presence of two asymmetry centers in their molecule, the compounds concerned can be prepared in the "threo" and the "erythro" configuration: mixtures of the "threo" and the "erythro" forms have also proven effective.

16 Claims, No Drawings

4-ALKYL-THIOPHENYL-ETHANOLAMINES, HAVING AN ACTIVITY THE CEREBRAL CIRCULATION, THE BLOOD PLATELET-AGGREGATION AND THE LIPENIA

This invention relates to a series of derivatives of alkyl-phenyl-sulphides, carrying, in the 4-position of the phenyl ring, a 1-hydroxyalkyl residue which is substituted in its 2-position by a basic aromatic, cycloaliphatic or heterocyclic radical, which can optionally be substituted.

Such derivatives, which can be defined as 4-alkyl-thiophenyl ethanolamines have the following general formula:

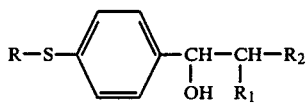

wherein:

R is a straight-chain alkyl or a branched alkyl containing from 1 to 4 carbon atoms.

$R_1$ is a straight-chain alkyl or a branched alkyl containing from 1 to 3 carbon atoms, and $R_2$ is a phenylamine or a cycloalkylamine radical having 5 or 6 carbon atoms, optionally carrying, as a substituent, a phenyl or a cyclohexyl radical, or $R_2$ can be a 1-piperazinyl residue carrying as a substituent, in its 4-position, a cinnamoyl or a cinnamyl radical, the latter radical being optionally substituted in its 3,4 and 5 positions, with 1, 2 or 3 methoxy, ethoxy, hydroxy, amino or nitro groups.

All of the compounds disclosed and claimed herein possess two chiral carbon atoms and thus they have two asymmetry centres, so that they can be split into two racemates which correspond to the "erythro" and the "threo" configuration, respectively. Such racemates, in their turn, can be split with the conventional procedures, such as the formation of diastereoisomers by salification with optically active acids, such as tartaric acid, separation of the mixtures of diastereoisomers thus obtained, with any conventional method, such as crystallization, distillation, chromatography and others, the base being then set free from the salts which have been so prepared.

As a result, the compounds prepared according to the present invention, may be used, either in the form of a mixture of their "erythro" and "threo" racemates, or in the form of their "erythro" racemate alone, or, also, in the form of their "threo" racemate, or, finally, in the form of either optical antipode of said two "erythro" and "threo" forms. Moreover, if $R_2$ is a substituted cycloalkylamine radical, the compounds correspondingly obtained may exhibit a "cis-trans" isomery.

In order to prepare the compounds in question, an alpha-bromo-4-alkyl-thiopropiophenone has been condensed with the preselected amine in the presence of either a mineral or an organic base, and the aminoketone thus obtained has been reduced to a secondary alcohol with boron and sodium hydride.

The same procedure has been adopted for prepating the piperazine derivatives, by condensing an alpha-bromo-4-alkyl-thiopropiophenone with the preselected N-cinnamoyl piperazine: the latter, in its turn, when heated in an appropriate solvent in the presence of boron and sodium hydride, has given a secondary alcohol with the N-cinnamoyl residue. Conversely, heating N-cinnamoyl piperazine in ethyl ether or tetrahydrofuran, in the presence of lithium and aluminium hydride, has given a secondary alcohol carrying the N-cinnamyl residue.

The compounds according to the present invention, when tested with the method by Born and Cross (J. Physiology, 168, 178 (1963), have proven to possess, both in vitro and ex-vivo, the property of inhibiting the blood-platelet aggregation caused by collagen or ADP in the blood of rats: the relevant results are tabulated in TABLE 1 herein.

The most active compounds, and, more particularly, the 1-(4-isopropylthiophenyl)-2-(4-cinnamoylpiperazine-1-yl)-1-propanol, in its "erythro" and "threo" forms, have shown, in addition, to be endowed with a considerable spasmolytic activity, in vitro, on isolated intestines of rats or Guinea pigs, and to inhibit the contractions caused by norepinephrine on the deferent duct according to the procedure by Barnett et al, Brit. J. Pharmacology, 34, 484 (1968) and to inhibit the contractions of isolated rat aorta according to the procedure by Godfraind and Kaba (Brit. J. Pharmacol., 36, 549 (1969). Also the contraction-promoting effect of the bivalent calcium ions on the depolarized aorta of rats has been inhibited, as ascertained with the procedure of Godfraind and Kaba (Arch. Int. Pharmacodyn., 196, 35 (1972).

The compounds according to the invention, furthermore, markedly decrease and, at certain dosages, annul, the total cholesterol increase, the triglyceride increase, the increase of the total lipids and phospholipids as caused in rats by treating them with Triton according to the procedure described by Moss and Dajani in Turner and Hobborn, Screening Methods in Pharmacology, Vol. 2, page 136. It has also been observed, still in rats, that the high-density lipoprotein level (HDL) increased, and this phenomenon corresponds, in men, to a preventative action against the formation of ateromata.

More particularly, the "threo" forms extend the time of resistance to anoxia if mice maintained in an atmosphere which is virtually devoid of oxygen, according to the test method by Hori et al. (Folia Pharm.Japonica, 76, 655 (1980).

The acute toxicity of the compounds made according to the invention is extremely low. TABLE 2 herein shows a comparison between the acute toxicity in mice and rats of the most active substances according to this invention and the acute toxicity of molecules used in the therapeutics and which, inter alia, possess only in part pharmacological properties akin to those of the substances disclosed herein.

A mixture of the two "erythro" and "threo" forms in proportions variable from 20% to 80%, preferably 50%, has exhibited all the pharmacological properties detected in each of the two individual forms: the toxicity on mice or rats was in the same order of magnitude as that of the "threo" form alone.

The invention will now be better illustrated by a few examples which describe in detail how the compounds of this invention can be prepared in practice.

EXAMPLE 1

Trans-1-(4-isopropylthiophenyl)-2-(4-phenylcyclohexylamino)-1-propanone 28.7 grams (g) of alpha-bromo-4-isopropylthiopropiophenone, 17.5 g of trans-4-phenylcyclohexylamine hydrochloride and 16.8 g of sodium bicarbonate have been refluxed for 6 hours in 200 mls of methanol. On completion of refluxing, the slurry has been allowed to cool, evaporated under vacuum to dryness and the residue has been taken up with water and extracted with ethyl ether. From the organic phase, after having washed it with water and dried over anh. sodium sulphate, there has been precipitated, with an alcoholic solution of hydrogen chloride, the hydrochloride of the amine concerned, which has been collected on a filter and recrystallized from dil. ethanol. The yield was 20 g and the melting point 240° C.

By the same procedure, but starting from 17.5 g of cis-3-phenylcyclohexylamine hydrochloride, there have been obtained 14 g of cis-1-(4-isopropylthiophenyl)-2-(3-phenylcyclohexylamino)-1-propanone hydrochloride, having a melting point of 234° C.

When using, as the starting compound, 17.5 g of 4-cyclohexylaniline hydrochloride, there have been obtained 23 g of 1-(4-isopropylthiophenyl)-2-(4-cyclohexylanilino)-1-propanone hydrochloride having a melting point of 175° C.

EXAMPLE 2

1-(4-isopropylthiophenyl)-2-(4-cinnamoylpiperazine-1-yl)-1-propanone 28.7 g of alpha-bromo-4-isopropylthiopropiophenone, 23.6 g of 1-cinnamoylpiperazine hydrochloride, and 16.8 g of sodium bicarbonate, have been refluxed in 200 mls of ethanol during 6 hours. On completion of refluxing, the mixture has been allowed to cool, evaporated to dryness in vacuum and the residue taken up with water and extracted with ethyl ether. From the organic phase, which had previously been washed with water, and dried over anh. sodium sulphate, the corresponding hydrochloride has been precipitated with an alcoholic solution of hydrogen chloride, and the precipitated hydrochloride has been collected on a filter.

The yield is 38 g and the melting point is 224° C. (recryst. from dil.ethanol).

By the same procedure, but starting from 34.3 g of 1-(3,4,5-trimethoxycinnamoyl)-piperazine hydrochloride, there have been obtained 45 g of 1-(4-isopropylthiophenyl)-2-[4-(3,4,5-trimethoxycinnamoyl)-piperazine-1-yl]-1-propanone hydrochloride, having a melting point of 142° C.

EXAMPLE 3

Trans-1-(4-isopropylthiophenyl)-2-(4-phenylcyclohexylamino)-1-propanol 41.8 g of trans-1-(4-isopropylthiophenyl)-2-(4-phenylcyclohexylamino)-1-propanone hydrochloride are slurried in 200 mls of methanol and treated in small increments with 11.4 g of sodium borohydride. On completion of the treatment, the slurry has been refluxed during 4 hours, allowed to cool and evaporated to dryness. The residue has been taken up with ethyl acetate and water, the organic layer has been separated, dried over anh. sodium sulphate and the base thus obtained has been converted into its hydrochloride. The yield is 27 g (from dil. ethanol) and the melting point is 238° C.

By the same procedure, but using as the starting product 41.8 g of 1-(4-isopropylthiophenyl)-2-(4-cyclohexylanilino)-1-propanone hydrochloride, there have been obtained 39 g of 1-(4-isopropylthiophenyl)-2-(4-cyclohexylanilino)-1-propanol hydrochloride, having a melting point of 104° C.

When, conversely, the starting reactant was 41.8 g of cis-1-(4-isopropylthiophenyl)-2-(3-phenylcyclohexylamino)-1-propanone hydrochloride, there were obtained 27 g of cis-1-(4-isopropylthiophenyl)-2-(3-phenylcyclohexylamino)-1-propanol hydrochloride, having a melting point of 244° C.

EXAMPLE 4

1-(4-isopropylthiophenyl)-2-(4-cinnamoyl-piperazine-1-yl)-1-propanol ("Threo" and "Erythro")

11.3 g (0.0267 mol) of 1-(4-isopropylthiophenyl)-2-(4-cinnamoylpiperazine-1-yl)-1-propanone in 160 mls of methanol have been treated in small increments, the temperature being meanwhile maintained between 20° C. and 25° C. with 1.51 g (0.04 mol) of NaBH4. On completion of such addition, the solution has been brought to a boil and thus maintained during 4 hours, whereafter it has been evaporated to dryness under a reduced pressure. The mixture of the "erythro" and the "threo" isomers has then been slurried in 200 mls of hot methanol, then cooled to 0° C.–5° C. and collected on a filter. The precipitate has been slurried in water, filtered once again and dried. The yield was 5.73 g of the expected compound and the melting point of it was 166° C.–167° C. The melting point of the corresponding hydrochloride was 201° C.–203° C.

The methanol used in the reaction, after a drop-filtration, has been acidified with chilled hydrochloric acid and the precipitate has been collected on a filter, washed with methanol and dried in oven, then reslurried in water, made alkaline with sodium carbonate and extracted with dichloromethane. The solvent has been evaporated off under vacuum and the residue has been taken up with a little ether, collected on a filter and oven dried. The melting point was 106° C.–108° C.; the melting point of the hydrochloride was 242° C.–243° C.

The scrutiny of the NMR spectra has permitted to establish that the isomer melting at 166° C.–167° C. has the "threo" configuration, so that the isomer melting at 106° C.–108° C. had the "erythro" configuration.

By adopting the same procedure, starting from 54.9 g of 1-(4-isopropylthiophenyl)-2-[4-(3,4,5-trimethoxycinnamoyl)-piperazine-1-yl]-1-propanone hydrochloride, there have been obtained 43 g of 1-(4-isopropylthiophenyl)-2-[4-(3,4,5-trimethoxycinnamoyl)-piperazine-1-yl]-1-propanol hydrochloride, "erythro" form, melting point 194° C.

EXAMPLE 5

1-(4-isopropylthiophenyl)-2-(4-cinnamylpiperazine-1-yl)-1-propanol ("erythro" form)

45.9 g of 1-(4-isopropylthiophenyl)-2-(4-cinnamoylpiperazine-1-yl)-1-propanone hydrochloride have been slowly added to a slurry of 8.36 g of lithium aluminium hydride in 900 mls of anh.tetrahydrofuran. After 2-hour refluxing, the reaction mixture has been cooled and the excess hydride has been decomposed first with ethyl acetate and then with about 80 mls of water. The as-formed precipitate has been collected on a filter and the filtrate has been evaporated to dryness, to produce an oily residue: the latter, taken up with ethyl ether, has been converted into the corresponding hydrochloride with the aid of a solution of hydrogen chloride in ethanol. The hydrochloride has been collected on a filter and recrystallized from a mixed aqueous-alcoholic solvent medium.

The yield is 30 g and the hydrochloride so produced has a melting point of 228° C.

By adopting the same procedure as outlined above, but using 54.9 g of 1-(4-isopropylthiophenyl)-2-[4-(3,4,5-trimethoxycinnamoyl)-piperazine-1-yl]-1-propanone hydrochloride as the starting compound, there have been obtained 26 g of 1-(4-isopropylthiophenyl)-2-[4-(3,4,5-trimethoxycinnamyl)-piperazine-1-yl]-1-propanol hydrochloride, in its "erythro" form, which has a melting point of 214° C.

TABLE 1

| | | | | Anti-blood-platelet aggregative action ex vivo against collagen | | |
|---|---|---|---|---|---|---|
| Compound No | R | $R_1$ | $R_2$ | Effect induced by the administration (oral route) of 150 micromols per kg b.w. | 600 | $LD_{50}$ mice intraperitoneally |
| 1 | $(CH_3)_2CH$ | $CH_3$ | $-N\underset{\diagdown\_\diagup}{\diagup^{\phantom{.}\diagdown}}N-CO-CH=CH-C_6H_5$ "erythro" | ++ | ++ | 920 |
| 2 | " | " | $-N\underset{\diagdown\_\diagup}{\diagup^{\phantom{.}\diagdown}}N-CO-CH=CH-C_6H_5$ (threo) | − | ± | >4000 |
| 3 | " | " | $-N\underset{\diagdown\_\diagup}{\diagup^{\phantom{.}\diagdown}}N-CO-CH=CH-C_6H_2 (3,4,5-OCH_3)$ | − | − | >400 |
| 4 | " | " | $-N\underset{\diagdown\_\diagup}{\diagup^{\phantom{.}\diagdown}}N-CH_2-CH=CH-C_6H_5$ | − | ++ | 300 |
| 5 | " | " | $-N\underset{\diagdown\_\diagup}{\diagup^{\phantom{.}\diagdown}}N-CH_2-CH=CH-C_6H_2 (3,4,5-OCH_3)$ | − | ++ | 75 |
| 6 | " | " | $-\underset{H}{N}-C_6H_5$ | ± | + | 400 |
| 7 | " | " | $-\underset{H}{N}-C_6H_4\text{-}2\text{-}C_6H_{11}$ | + | + | >400 |
| 8 | " | " | $-\underset{H}{N}-C_6H_4\text{-}3\text{-}C_6H_{11}$ | + | + | 500 |
| 9 | " | " | $-\underset{H}{N}-C_6H_4\text{-}4\text{-}C_6H_{11}$ | − | − | >400 |
| 10 | " | " | $-\underset{H}{N}-C_6H_5$ | ± | + | >400 |
| 11 | " | " | $-\underset{H}{N}-C_6H_{10}\text{-}C_6H_5$ | ± | + | >400 |

TABLE 1-continued

Anti-blood-platelet aggregative action ex vivo against collagen

| Compound No | R | $R_1$ | $R_2$ | Effect induced by the administration (oral route) of 150 micromols per kg b.w. | Effect induced by the administration (oral route) of 600 micromols per kg b.w. | $LD_{50}$ mice intraperitoneally |
|---|---|---|---|---|---|---|
| 12 | " | " | (−NH−cyclohexyl−C₆H₅) | — | — | 80 |
| 13 | " | " | (−NH−cyclohexyl−C₆H₅) | ± | ++ | 150 |
| Suloctidil | — | — | — | ++ | ++ | 32.5 |

TABLE 2

ACUTE TOXICITY TESTS

| | MICE $LD_{50}$ mg/kg b.w. (in brackets:micromol/kg equivalent) | | RATS $LD_{50}$ mg/kg b.w. (in brackets:micromol/kg equivalent) | |
|---|---|---|---|---|
| TESTED PRODUCTS | intraperitoneally | orally | intraperitoneally | orally |
| 1-(4-isopropylthiophenyl)-2-(4-cinnamoylpiperazine-1-yl-1-propanol-'Threo' form | ≧ 4000 (=9421) | > 5000 (=11,776) | > 4000 (=9421) | > 4000 (=9421) |
| Same as above, "erythro" form | 920 (=2167) | (°) 3650 (=7917) | > 3000 (=7066) | > 4000 (=9421) |
| Fiducial limits | 782–1082 (=1842–2548) | 3166–4208 (=6867–9127) | — | — |
| Slope (fid. lim.) | 1.36 (1.14–1.47) | 1.25 (1.10–1.42) | — | — |
| Suloctidil | 32.5 (=96.3) | 2250 (=6666) | 47 (=139) | 1780 (=(5273) |
| Fiducial limits | 26.8–39.4 (=70.4–116.7) | 2016–2511 (=5972–7439) | 32–69 (=94.8–204.4) | 1603–1976 (=4749–5854) |
| Slope (fiducial limit) | 1.55 (1.33–1.82) | 1.24 (1.18–1.30) | 1.86 (1.42–2.44) | 1.18 (1.13–1.22) |
| Cinnarizine | > 2000 (=5427) | > 4000 (=10.885) | > 2000 (=5427) | > 4000 (=10.885) |
| Flunarizine (°) | 355 (=776) | 585 (=1278) | 425 (=929) | 2180 (=4766) |
| Fiducial limits | 325–386 (=712–845) | 498–687 (=1088–1502) | 332–543 (=726–1187) | 1714–2773 (=3747–6062) |
| Slope (fid. lim.) | 1.10 (1.05–1.16) | 1.29 (1.18–1.42) | 1.48 (1.20–1.83) | 1.47 (1.21–1.78) |
| Clofibrate | 660 (=2719) | 1620 (=6675) | 1250 (=5150) | 2300 (=9476) |

(°) The corresponding hydrochloride has been used

We claim:

1. A 4-alkyl-thiophenyl-ethanolamine having the formula:

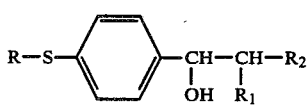

wherein:
R is a straight-chain alkyl or a branched-chain alkyl having from 1 to 4 carbon atoms,
$R_1$ is a straight-chain alkyl, or a branched-chain alkyl having from 1 to 3 carbon atoms, and
$R_2$ is a 1-piperazinyl carrying as a substituent in its 4-position, a cinnamoyl or a cinnamyl radical or a cinnamoyl or cinnamyl radical having a substituent in at least one of its 3, 4, and 5 positions, said substituent being a methoxy, ethoxy, hydroxy, amino or nitro group.

2. A 4-alkyl-thiophenyl-ethanolamine according to claim 1 where $R_2$ is a 1-piperazinyl carrying as a substituent in its 4-position a cinnamoyl radical or a cinnamoyl radical having a substituent in at least one of its 3, 4, and 5 positions, said substituent being a methoxy, ethoxy, hydroxy, amino, or nitro group.

3. A 4-alkyl-thiophenyl-ethanolamine according to claim 1 free of substituents on the cinnamoyl or cinnamyl radical.

4. A 4-alkyl-thiophenyl-ethanolamine according to claim 1 having 1 to 3 methoxy groups as the sole substituents on the cinnamoyl or cinnamyl radical.

5. A 4-alkyl-thiophenyl-ethanolamine according to claim 4 having 3 methoxy groups as the sole substituents on the cinnamoyl or cinnamyl radical.

6. A 4-alkylthiophenylethanol according to claim 1 having 1 to 3 methoxy or ethoxy groups as the sole substituents on the cinnamoyl or cinnamyl radical.

7. A 4-alkylthiophenylethanol according to claim 6 which is 1-(4-isopropylthiophenyl)-2-[4-(3,4,5-trimethoxycinnamoyl)-piperazine-1-yl]-1-propanol in its erythro and threo forms.

8. A 4-alkylthiophenylethanol according to claim 6 which is 1-(4-isopropylthiophenyl)-2-[4-(3,4,5-trimethoxycinnamyl)-piperazine-1-yl]-1-propanol in its erythro and threo forms.

9. 1-(4-isopropylthiophenyl)-2-(4-cinnamoylpiperazine-1-yl)-1-propanol, erythro form.

10. 1-(4-isopropylthiophenyl)-2-(4-cinnamoylpiperazine-1-yl)-1-propanol, threo form.

11. 1-(4-isopropylthiophenyl)-2-(4-cinnamyl-piperazine-1-yl)-1-propanol, threo form.

12. A process of imparting an anti-blood platelet aggregation action to an animal comprising administering to the animal an amount of a compound of claim 1 effective to impart said anti-blood platelet aggregation action.

13. A process of improving the cerebral circulation in an animal comprising administering to the animal an amount of a compound of claim 1 effective to improve the cerebral circulation.

14. A process of preventing lipemia in an animal comprising administering to the animal an amount of compound of claim 1 effective to prevent lipemia.

15. A process of preventing the formation of ateromata in an animal comprising administering to the animal an amount of a compound of claim 1 effective to prevent the formation of ateromata.

16. A process of preventing anoxia in an animal comprising administering to the animal an amount of a compound of claim 1 effective to prevent anoxia.

* * * * *

UNITED STATES PATENT AND TRADEMARK OFFICE
CERTIFICATE OF CORRECTION

PATENT NO. : 4,587,248

DATED : May 6, 1986

INVENTOR(S) : Giorgio Cantarelli et al.

It is certified that error appears in the above-identified patent and that said Letters Patent is hereby corrected as shown below:

On the Title Page add:

-- [73] Assignee: Maggioni Farmaceutici S.P.A., Milan, Italy --.

Signed and Sealed this

Twenty-fourth Day of March, 1987

Attest:

DONALD J. QUIGG

*Attesting Officer*   *Commissioner of Patents and Trademarks*